United States Patent [19]
Petralli

[11] Patent Number: 5,011,286
[45] Date of Patent: Apr. 30, 1991

[54] MULTISENSOR PARTICLE COUNTER UTILIZING A SINGLE ENERGY SOURCE

[75] Inventor: Louis J. Petralli, Grants Pass, Oreg.
[73] Assignee: Met One, Inc., Grants Pass, Oreg.
[21] Appl. No.: 389,061
[22] Filed: Aug. 3, 1989
[51] Int. Cl.[5] .............................. G01N 21/00
[52] U.S. Cl. ..................... 356/343; 356/338
[58] Field of Search ......................... 356/335–343, 356/39, 73, 244; 250/564, 565

[56] References Cited

U.S. PATENT DOCUMENTS

| | | | |
|---|---|---|---|
| 3,798,465 | 1/1989 | Knollenberg | 356/336 |
| 4,134,679 | 1/1979 | Wertheimer | 356/336 |
| 4,387,993 | 6/1983 | Adrian | 356/336 |
| 4,448,500 | 10/1985 | Wyatt et al. | 356/336 |
| 4,639,137 | 1/1987 | Hagan et al. | 356/343 |
| 4,726,681 | 2/1988 | Webb | 356/343 |
| 4,728,190 | 3/1988 | Knollenberg | 356/336 |

OTHER PUBLICATIONS

Fukushima, N., et al., "A New Particle Counter (UPC) and its Performance," 9th ICCCS Proceedings 1988, Osaka, Japan, p. 220.

Primary Examiner—Richard A. Rosenberger
Assistant Examiner—Hoa Pham
Attorney, Agent, or Firm—Schneck & McHugh

[57] ABSTRACT

An apparatus and method for particle detection which includes a plurality of sample regions. A sensor body has internal walls which define spaced apart sample regions, with each sample region having an inlet port and an exhaust port. An aggregate sample flow is divided into partial flows which are directed from the inlet port to the exhaust port of an associated sample region. A light source, typically a laser, is positioned to project an incident beam along a light path which intersects each of the partial sample flows through the sample regions. Particles contained within the partial sample flows scatter light as the particles pass through the incident beam. The light from a sample region is directed to a photodetector which provides a signal corresponding to the sensed light. Particle detection in each sample region is operationally independent of the others, but the information is combined to provide a total particle count of the aggregate sample flow. Alternatively, the apparatus may be utilized to provide simultaneous particle detection of separate sources of particle-bearing gas. For example, adjacent clean room areas may be monitored channelling separate sample flows directly into separate inlet ports of adjacent sample regions.

18 Claims, 4 Drawing Sheets

MULTISENSOR PARTICLE COUNTER UTILIZING A SINGLE ENERGY SOURCE

TECHNICAL FIELD

The present invention relates generally to particle size measurement apparatus and particularly to apparatus for determining the size and concentration of particles in a fluid.

BACKGROUND ART

Devices which measure and count particles in a fluid are well known. Such devices are employed, for example, by semiconductor wafer manufacturers to monitor the extent of airborne particulate matter in a clean room. Pharmaceutical manufacturers employ such devices for the detection and control of foreign particles. To a lesser extent of accuracy, smoke detectors also measure particle concentration.

One method of particle detection is the light blockage particle counting, or light obscuration, method. Light obscuration sensors work on the principle of the casting of a shadow onto a photodetector as a flow of particle-laden fluid is directed through a light beam generated by an incandescent lamp. A more sensitive method is the light scattering method. As a particle passes through a light beam, the particle scatters light. For a stationary particle, the amount of scattered light is a function of the particle size, the wavelength and intensity of the incident light, and the difference between the light scattering properties of the particle and the surrounding medium. A laser source may be used to generate the light beam and the scattered light is sensed by a detector which provides readable signals indicative of particle size.

In addition to those factors listed above, which enter into the determination of the amount of light scattered by a particle, other factors must be considered where the particle is not stationary but rather is contained within a sample flow of fluid. To detect all particles in a sample flow, the flow must have a cross section sufficiently small to remain completely within the view volume of a detection device. In applications such as clean room monitoring, the flow rate of a given volume is typically a standard, for example, one cubic foot per minute. Consequently, the minimum velocity of the particle-laden sample flow is fixed by the view volume of the incident beam.

The velocity of a sample flow determines the time in which a particle remains within the view volume of the detection device. This time is important for two reasons. Firstly, the quantity of light which a given particle can scatter while in the view volume is inversely proportional to particle velocity and directly proportional to particle size. Increasing the velocity of a particle by a factor of two results in a halving of the time span in which the particle travels through the view volume, thereby decreasing the quantity of scattered light by half.

Secondly, the pulse width plays an important part in optimizing the signal-to-noise ratio of a particle detector. The minimum particle velocity fixes the minimum time in which a particle travels through the view volume of the incident beam, which, in turn, governs the minimum pulse width which is produced by the detector electronics. Fast pulses require the electronics high frequency response corner to increase. Raising the high frequency response corner increases the amount of amplifier noise, thus degrading the signal-to-noise ratio of the particle counter. However, since particle velocity through a view volume is typically high, fast pulses are produced, so that the high frequency noise is less likely to be rejected.

One answer to increasing the aggregate amount of light scattered by a particle while in the view volume and simultaneously raise the minimum expected pulse width, is to reduce the velocity of the sample flow and spread out the sample time. However, sample flows of a given volume are typically specified by the industry.

Another possible answer is to increase the view volume of the device. The maximum view volume, however, is limited by the light source and the scattered light collection optics.

It is an object of the present invention to provide an apparatus for detecting particles, wherein the aggregate amount of light scattered by a given particle in a sample volume is significantly increased, and wherein the minimum expected pulse width caused by a particle traveling through a view volume is likewise increased.

SUMMARY OF THE INVENTION

The above object has been met by an apparatus which provides a plurality of parallel sample flows, say a number n where $n \geq 2$, so as to permit any given particle to spend n times as long in a detection, or sample, area. Thus, the aggregate scattered light increases by a factor of n and the minimum pulse width is reduced by $1/n$. This is accomplished by utilizing a single light source, typically a laser, to illuminate a plurality of sample areas. A single sample flow progressing at a known or fixed rate is divided into a plurality of slower sample flows which are directed to intersect the incident beam of the light source at spaced apart sample areas. Detection of particles at each of the sample areas is performed independently, whereafter the information can be combined to provide a particle count for the original, single sample flow.

The apparatus includes a sensor body having internal walls which define a plurality of sample regions, with each sample region having an inlet port and an exhaust port. Adjacent sample regions are joined by passageways. The laser directs an incident beam along a light path through each of the sample regions via the passageways which join the adjacent sample regions. The aggregate sample flow enters a manifold which divides a flow into a plurality of partial sample flows. Each partial sample flow enters an associated sample region through the inlet port and exits through the exhaust port.

Particles within a partial sample flow cause a scattering of radiation as the incident beam strikes the particles. A concave spherical reflector and a lens system act together to collect the scattered radiation and direct the radiation to a photodetector. The photodetector senses the energy of the collected radiation and outputs a signal corresponding to the sensed energy. The signal can be used to determine a particle size and a particle count.

An advantage of the present invention is that the lower limit of particle size detection is reduced. One factor in determining the parameter of particle size is the speed of the particle passage through the sample region. A slower moving particle stays within a sensing region for a greater period of time so that the total amount of light scattered by the particle is increased. The increase in scattered light increases the likelihood that presence of the particle will be detected. Another advantage is that because the pulse width from the photodetector is equal to the time in which a particle exists within a sample region, the minimum expected pulse width is increased by providing a plurality of partial sample flows rather than a single sample flow. Increasing the minimum expected pulse width permits an increase in the signal-to-noise ratio by reducing the high frequency bandwidth requirement.

Altering the configuration so as to achieve a second embodiment that allows multiple separate sample flows to be each individually detected, permits the present invention to provide a more compact, more economical detector than the use of multiple separate detectors. It also permits particle monitoring to occur in real time, as opposed to serially time-sampling a manifold of flows. For example, adjacent clean room areas or different chambers of processing equipment can be simultaneously monitored. Moreover, particle dispersement and propagation patterns can be detected. The laser is typically the most costly element of a particle detector, but by using a single laser to illuminate a plurality of sample areas, a more powerful and sophisticated laser can be used than would be economically possible for individual particle counter applications.

BRIEF DESCRIPTION OF THE DRAWINGS

FIG. 2a is a rear cross-sectional view of the sensor of FIG. 2 taken along lines 2a—2a.

FIG. 3a is a top sectional view of the sensor of FIG. 3 taken along lines 3a—3a.

BEST MODE FOR CARRYING OUT THE INVENTION

Figure 1:
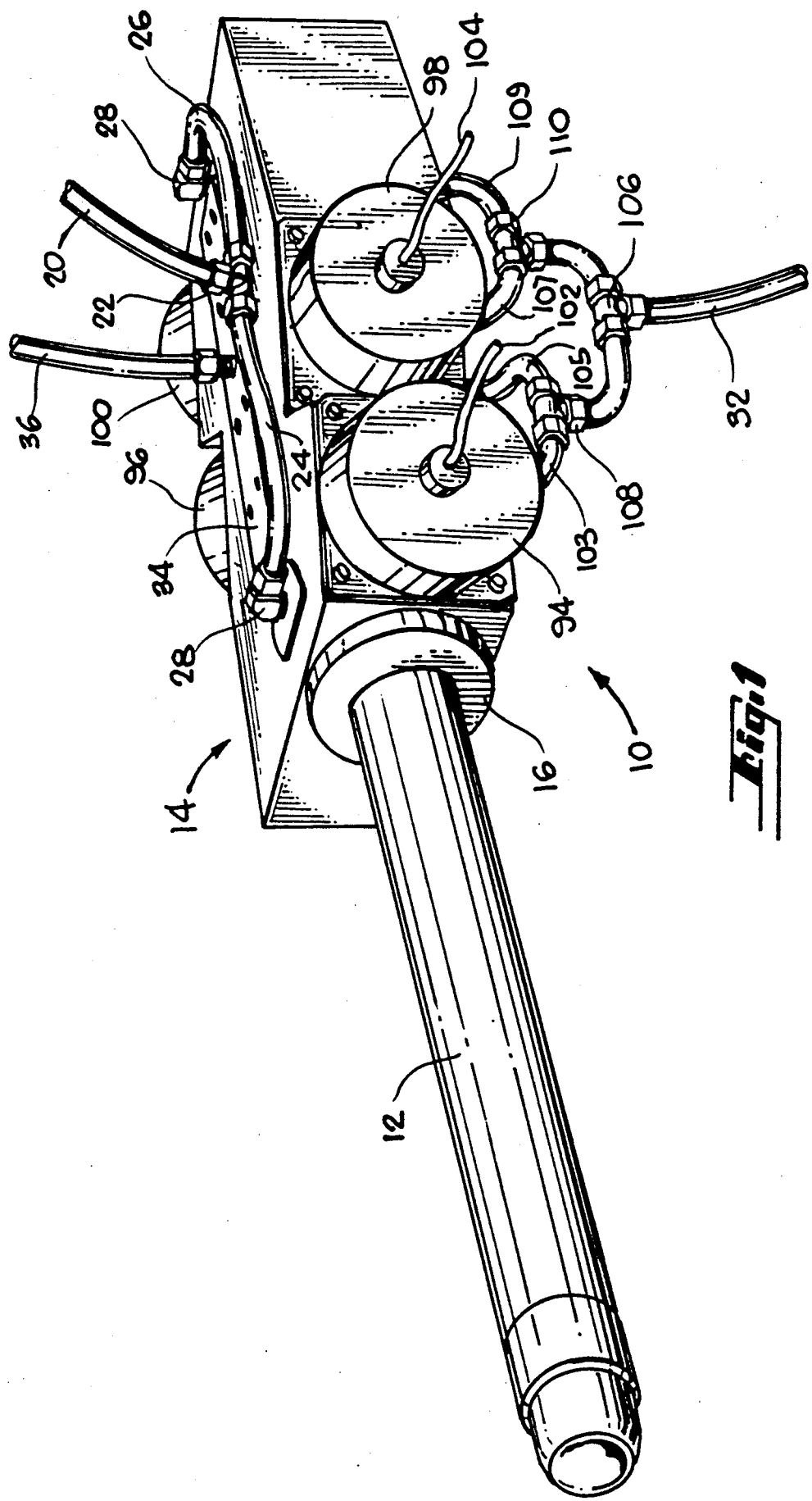
FIG. 1 is a perspective view of a multiport split flow particle sensor in accord with the present invention.
Figure 2:
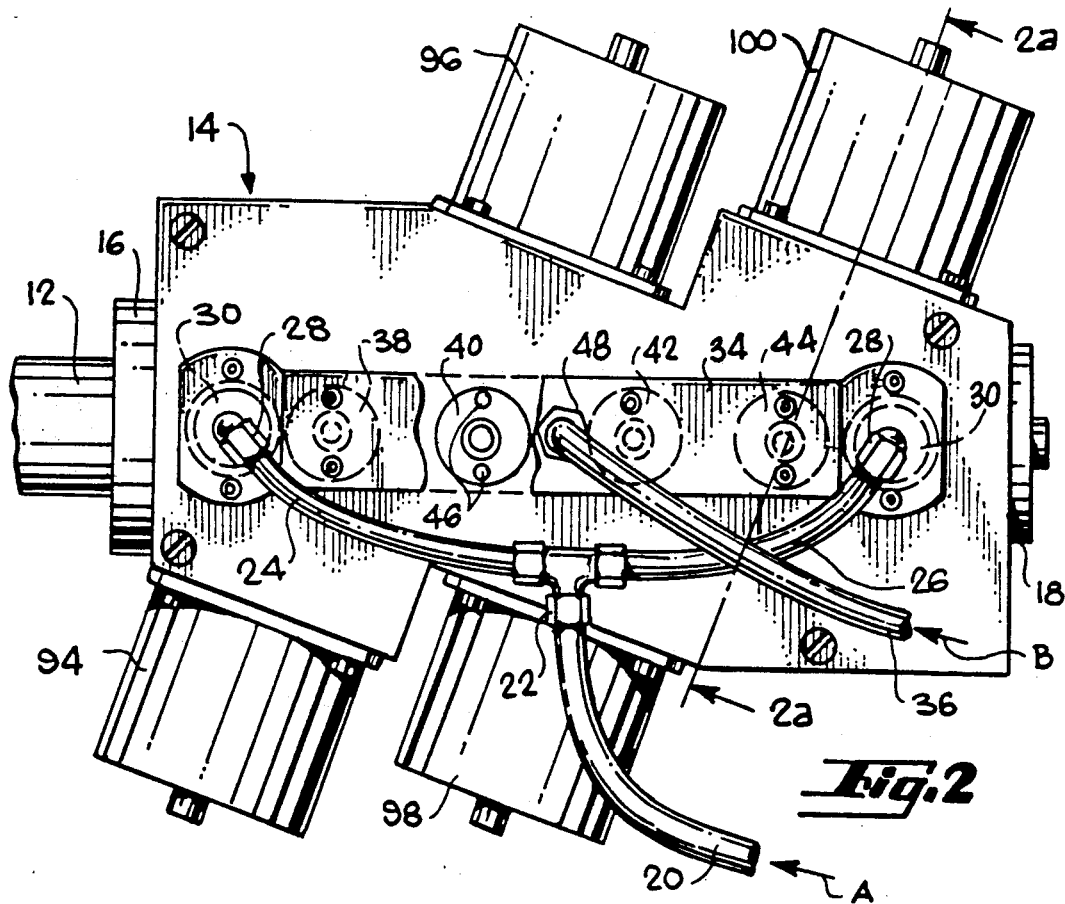
FIG. 2 is a top view of the sensor of FIG. 1.

With reference to FIGS. 1 and 2, a multiport split flow particle sensor 10 includes a plasma tube 12 and a sensor body 14. The sensor 10 is an open cavity laser system combined with a solid state diode to provide an electrical signal having a characteristic corresponding to the size of a particle in a sample flow. The sensor 10 utilizes a HeNe laser, but this is not critical. The plasma tube is fixed to the sensor body at an annular mount 16. At the forward end of the sensor body 14, nearest the plasma tube, is a Brewster window and a light trap, not shown. At the opposite end is a laser resonator mirror and another light trap, with a mirror mount 18 being shown in FIG. 2. Additional light traps, not shown, are utilized at each light passageway described below.

A purge air system is used to prevent contamination of the laser optical parts. A low flow of clean air enters a purge inlet tube 20, as shown by arrow A, and is divided at a T-shaped restrictor 22. The flow of air progresses through tubes 24 and 26 to fittings 28 which are fixed to the sensor body 14 at purge nozzles 30. The diameter of the passage to the T-shaped restrictor 22 determines the velocity of flow of the purged air. A vacuum source connected to a sample exhaust tube 32, shown in FIG. 1, also draws the clean air from the purged inlet tube 20 so as to keep the laser optics clean.

Figure 2A:
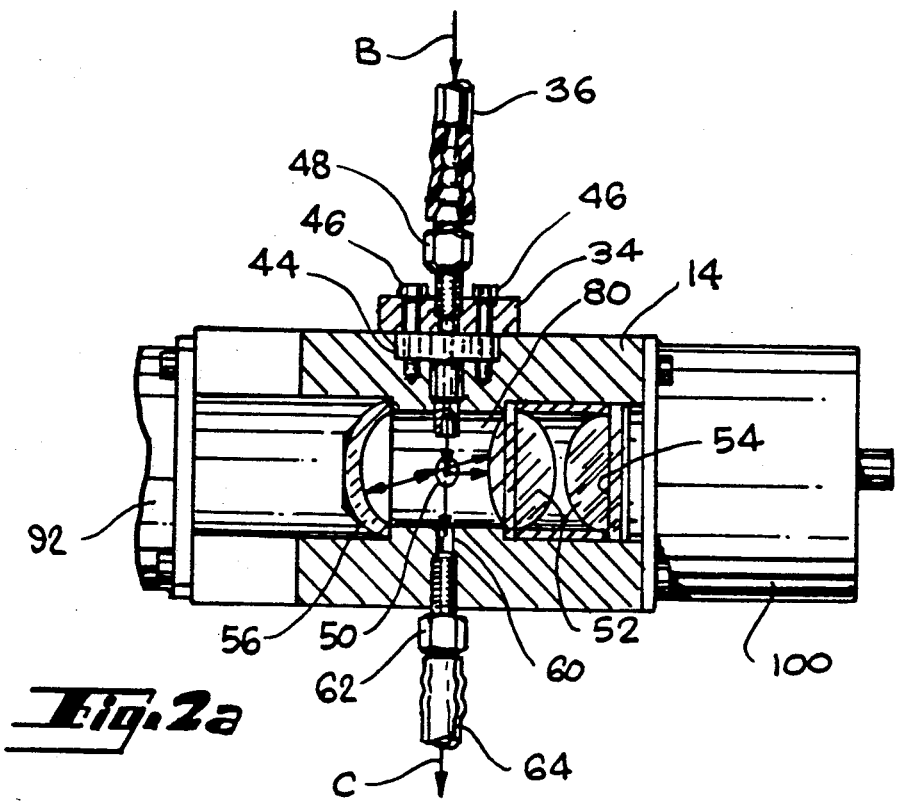

Referring now to FIGS. 2 and 2a, an aggregate sample flow, indicated by arrow B, is drawn into an inlet manifold 34 from an aerosol inlet tube 36. Particle-bearing gas, typically air, enters the inlet manifold 34 and is split once and then again to provide four separate flows. The four separate partial sample flows are received at four nozzles 38, 40, 42 and 44 which are held to the sensor body by Allenhead screws 46. Each nozzle 38-44 has an air passageway.

The structure of the passageways for particle-bearing gas through the inlet manifold 34 is an important feature in obtaining an accurate reading of a particle count in a clean room or the like. Large particles which strike the walls of a passage can be broken into smaller particles, thereby creating an inaccurate particle count. Moreover, where, as here, a flow is divided into individual passages, if unless downstream passages have the same cross-sectional area as the original, there will be changes in temperature, pressure and velocity. A change in pressure may cause evaporation or condensation of vapors, thereby jeopardizing the particle count. A decrease in velocity may result in larger particles settling out. Therefore, the inlet manifold 34 is structured such that the downstream passages have a total cross-sectional area which is equal to the cross-sectional area of the inlet. Moreover, the transition from one cross-sectional area to another is made as smooth as possible to reduce particle breakage and turbulence. Any change in direction at a flow split is as small as mechanically possible, so as to reduce the risk of particle breakup.

An externally-threaded fitting 48 is secured to the inlet manifold 34 at one end and is friction fit to the aerosol inlet tube 36 at the opposite end. The screws 46 secure both the inlet manifold 34 and the nozzle 44, as best seen in FIG. 2a. The nozzle 44 acts as an inlet port for the particle-bearing gas into a sample region of the sensor body 14. As indicated by the series of four arrows beginning with intake arrow B and terminating with exhaust arrow C, the partial sample flow through the sensor body 14 intersects the incident beam, represented by ellipse 50, of the laser. The sample area is that area of intersection between the incident beam 50 and the partial sample flow. A particle contained within the partial sample flow causes a scattering of light as the particle passes through the incident beam. Light is scattered in many directions. A portion of the scattered light is directed at a lens system 52 which is secured in position by a cylindrical member 54. A second portion of the scattered light is reflected from a concave spherical reflector 56 which reflects the energy back through the sample area to the lens system 52. The lens system 52 focuses the radiation to a photodetector within the detector cover 100. The photodetector, not shown, provides an electrical signal which has a characteristic corresponding to the energy received from the lens system. The partial sample flow exits the sample area through an exhaust port 60 that leads to an externally-threaded fitting 62 which is press fit to a hose 64.

Figure 3:
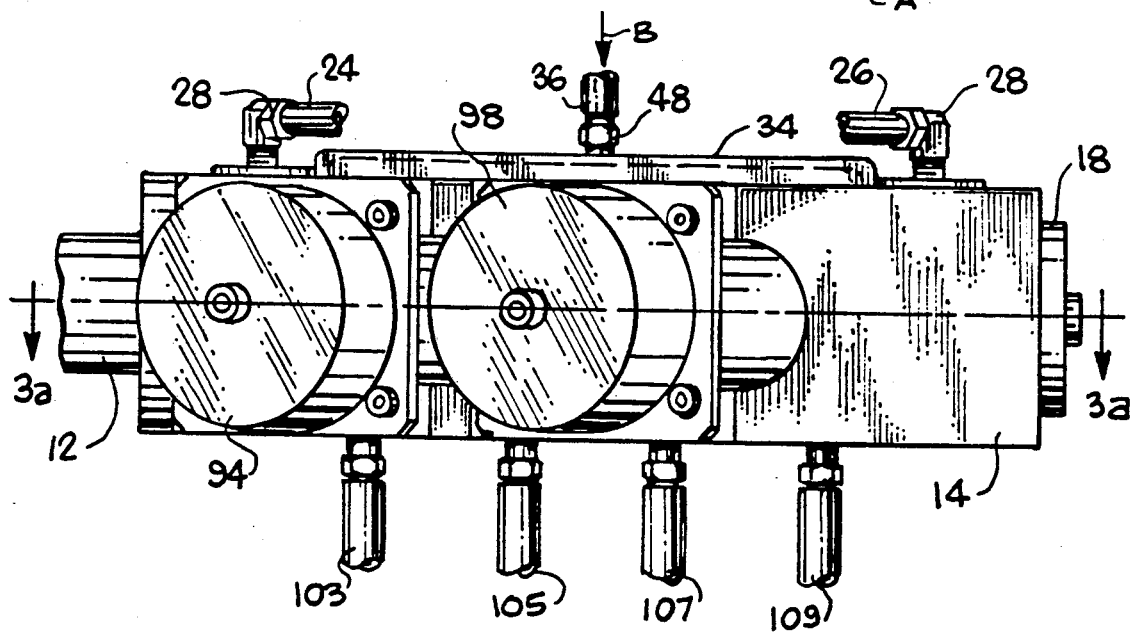
FIG. 3 is a side view of the sensor of FIG. 2.
Figure 3A:
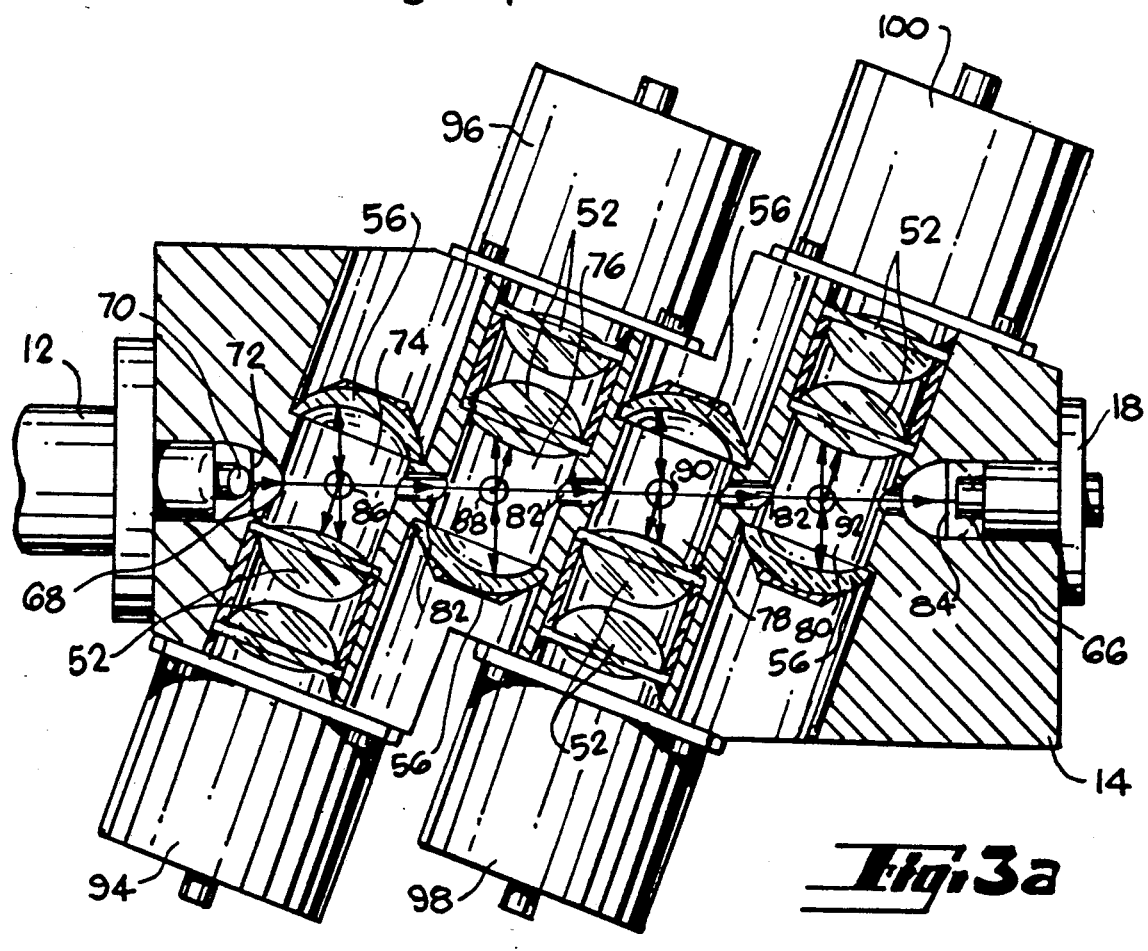

Referring now to FIGS. 3 and 3a, a laser beam is projected from the plasma tube 12 and travels to a laser resonator mirror 66 at the rear of the sensor body 14. The mirror 66 is housed within the mirror mount 18. The incident beam axis is represented by line 68. The incident beam exits from a Brewster window 70 and passes through a light trap 72. Four cavities 74, 76, 78 and 80 are disposed along the incident beam axis 68, with adjacent cavities being joined by light passageways 82. A light trap 84 is located at the rear of the sensor body 14 immediately preceding the laser resonator mirror 66. Additional light traps, not shown, are utilized at each light passageway 82.

Each of the cavities 74–80 is associated with a separate sample area. The sample area is that area in which the laser beam intersects one of the four partial sample flows. The partial sample flows are represented by circles 86, 88, 90 and 92 at the center of the associated cavity. The incident beam axis 68 is aligned to pass through the center of each sample flow 86–92. The laser beam itself has a diameter which essentially fills the sample area.

A partial sample flow of particle-bearing fluid passes through the laser beam, causing a scattering of light as particles move through the beam. The scattered light in a cavity is reflected by the concave spherical reflector 56 and is directed to a photodetector by the associated lens system 52. The photodetectors, not shown, are housed within detector covers 94, 96, 98 and 100. Each photodetector produces an electrical signal having a characteristic corresponding to the intensity of the scattered light collected from the associated cavity 74–80. As illustrated in FIG. 1, wires 102 and 104 are utilized for outputting signals from the detectors. High speed signal processing and data management then convert the scattered light measurement into particle size and number readings. The four measurements of scattered light are combined in a manner to provide a particle count for the aggregate sample flow which enters through the aerosol inlet tube 36.

As noted above, the sample exhaust tube 32 is connected at a downstream end to a vacuum source. As shown in FIG. 1, the exhaust tube is connected at an upstream end to a first T-shaped member 106 that, in turn, is in fluid communication with second and third T-shaped members 108 and 110 to supply sub-atmospheric pressure, via lines 103, 105, 107 and 109, to each of the cavities that include the sample areas.

In operation, an aggregate sample flow enters the aerosol inlet tube 36. This aggregate sample flow is typically at a standardized flow rate, e.g. 1 cubic foot per minute. The aggregate sample flow is divided into four partial sample flows by the inlet manifold 34. These partial sample flows are represented by circles 86–92 in FIG. 3a. The intersections of the partial sample flows with the laser beam traveling along incident beam axis 68 define four independent sample areas. Particles that enter the sample areas scatter light which is reflected, collected and sensed to provide electrical signals characterized by the sensed energy. Again, the four readings are then combined. A large particle scatters a greater amount of light than does a small particle. Consequently, the pulse which is produced by a large particle traveling through a sample area has a greater amplitude. Conversely, a small particle is capable of causing only a small amplitude pulse, and therefore the presence of a relatively small particle is more likely to go undetected. By dividing the aggregate sample flow into a plurality of sample flows, the velocity through the area in which particles are detected is reduced. Since a particle causes a scattering of light during the entire time that the particle is illuminated by the laser beam, the decrease in velocity results in an increase in the total quantity of scattered light. This has two effects. Firstly, the increase in total scattered light enhances the possibility of relatively small particles being detected. Thus, the lower limit of particle detection is reduced. Secondly, because particles are present within the sample area for a greater time span, the minimum expected pulse width is increased. A flow rate which is decreased by a factor of four results in any particle spending four times as much time within a sample area. This quadruples the length of the detection pulse. The increase in the minimum expected pulse width allows amplifiers to have a reduced noise bandwidth, thereby improving the signal-to-noise ratio.

Figure 4:
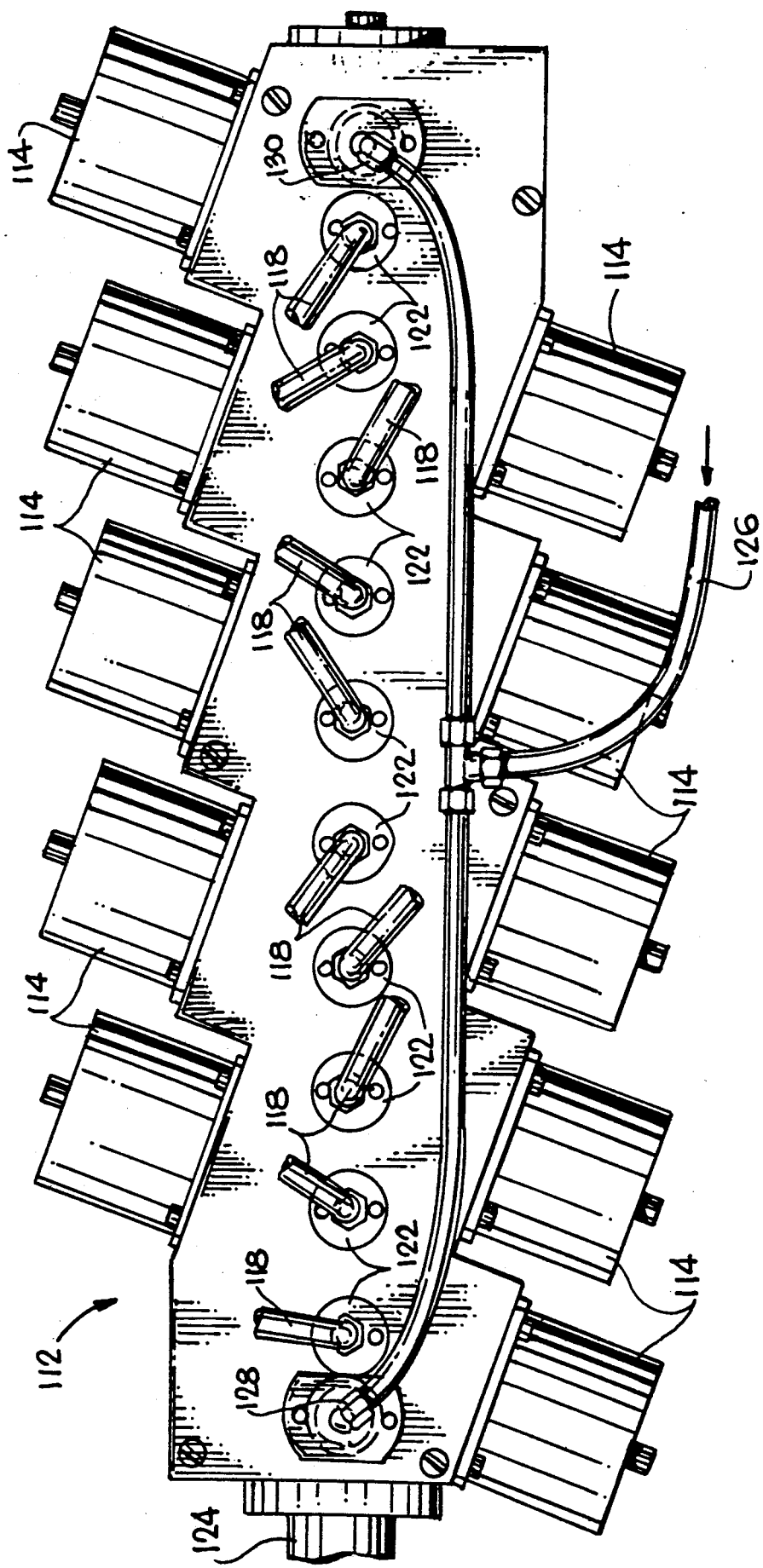
FIG. 4 is a second embodiment of a multiport separate flow particle sensor in accord with the present invention.

FIG. 4 shows a second embodiment of the present invention. The multiport separate flow particle sensor 112 includes a total of ten detectors 114, rather than four. Each detector 114 is independent of the remaining detectors. Separate sample flows enter individual inlet nozzles 122 via an associated tube 118. Each separate sample flow intersects a laser beam generated by a plasma tube 124. The separate sample flows are independently monitored by the associated detector 114, whereafter the information can be inspected individually. The sensor 112 includes a purge inlet tube 126 which provides a stream of air to opposed fittings 128 and 130 for maintaining the cleanliness of the optics associated with the laser beam.

The separate flow particle sensor 112 may be utilized to simultaneously monitor adjacent clean room or different chambers of processing equipment. Moreover, the particle sensor 112 can be used for detecting particle dispersion and propagation patterns.

While the present invention has been described as providing parallel partial sample flows, this is not critical. The sample flows can be at an angle relative to each other. Moreover, the detectors have been illustrated as being at a seventy degree angle relative to the incident beam. Other angles are possible, with the detector typically at an angle within the range of fifty degrees to ninety degrees.

I claim:

1. An apparatus for the detection of individual particles in a fluid comprising:
    a sensor body having a plurality of sample regions therein, adjacent sample regions being joined by an optical passageway,
    a light source disposed with respect to said sensor body to project an incident beam along a light path through each of said sample regions via said optical passageway joining adjacent sample regions,
    means for directing a plurality of generally identical sample flows of particle-bearing gas of substantially identical humidity into the sample regions such that each sample gas flow passes through said light path, none of said sample gas flows being reference flows with respect to the other sample gas flows, and
    a plurality of detector means for sensing scattered light caused by impingement of individual particles along said light path and for providing a signal corresponding to the quantity of sensed light, thereby allowing counting of said particles, said detector means being disposed with respect to said sensor body such that each detector means is substantially limited to sensing of scattered light from an operationally separate sample region.

2. The apparatus of claim 1 wherein said sensor body includes an inlet port and an outlet port to each of said sample regions, said inlet ports and said exhaust ports are aligned to provide spaced apart parallel sample flows across said light path.

3. The apparatus of claim 1 wherein said means for directing sample flows includes a manifold having a single inlet passageway and a plurality of outlet passageways, said outlet passageways directed to provide sample flows into each of said sample regions.

4. The apparatus of claim 1 wherein each detector means includes a photodetector and wherein said fluid is a gas.

5. The apparatus of claim 1 wherein said sample regions are linearly arranged and are joined by a longitudinal passageway which defines said light path.

6. The apparatus of claim 1 wherein said light source is a laser.

7. An apparatus for detecting particles in a sample volume of fluid comprising:
  a light source for projecting an incident beam along a light path;
  a plurality of channeling means for dividing a sample flow of gas to form a plurality of separate non-referenced sample flows of substantially identical humidity intersecting said light path, each intersection of said light path with a sample gas flow defining a sample region and causing a scattering of radiation by particles suspended in the associated sample gas flow, and
  a plurality of detector means for collecting scattered radiation and for outputting a signal in response thereto, said plurality of detector means being disposed with respect to said channeling means such that each detector means optically measures particles in only one sample region.

8. The apparatus of claim 7 wherein each channeling means is spaced apart from an adjacent channeling means to define spaced apart sample regions.

9. The apparatus of claim 8 wherein each channeling means includes conduits disposed to provide parallel sample flows across said light path.

10. The apparatus of claim 8 wherein each channeling means includes a passageway through a manifold having a single inlet and a plurality of outlets directed to provide parallel sample flows of fluid across said light path.

11. The apparatus of claim 7 wherein said light source is a laser.

12. The apparatus of claim 7 wherein said detector means includes a photodetector and includes optics to collect said scattering of radiation and to focus said collected radiation onto said photodetector.

13. The apparatus of claim 12 wherein said photodetector is a photodiode.

14. The apparatus of claim 12 wherein each detector means is at an angle relative to said light path, said angle being in the range of fifty degrees to ninety degrees, inclusively.

15. A method of detecting particles suspended in a gas comprising:
  splitting an aggregate sample flow of particle-bearing gas into a plurality of substantially identical parallel partial sample flows,
  traversing said substantially identical partial sample flows with a single incident beam to cause radiation scattering upon impingement of particles suspended in said partial sample flows with said incident beam,
  collecting and sensing a portion of said scattered radiation, and
  outputting a signal for each of said partial sample flows wherein each signal has a characteristic corresponding to the quantity of sensed scattered radiation.

16. The method of claim 15 wherein said signals are of the type to be combined to determine the aggregate concentration of particles ion said aggregate sample flow.

17. The method of claim 15 wherein said step of traversing said partial sample flows with an incident beam is performed by a laser beam generated by a laser source.

18. An apparatus for the detection of particles in a fluid comprising:
  a sensor body having at least four sample regions therein, adjacent sample regions being joined by an optical passageway,
  a light source disposed with respect to said sensor body to project an incident beam along a light path through each of said sample regions via said optical passageway joining adjacent sample regions,
  means for directing a plurality of sample flows of particle-bearing fluid of substantially identical humidity into the sample regions such that each sample flow passes through said light path, and
  a plurality of detector means for sensing scattered light caused by impingement of particles along said light path and for providing a signal corresponding to the quantity of sensed light, said detector means being disposed with respect to said sensor body such that each detector means is substantially limited to sensing of scattered light from an operationally separate sample region.

* * * * *